Figure 1:
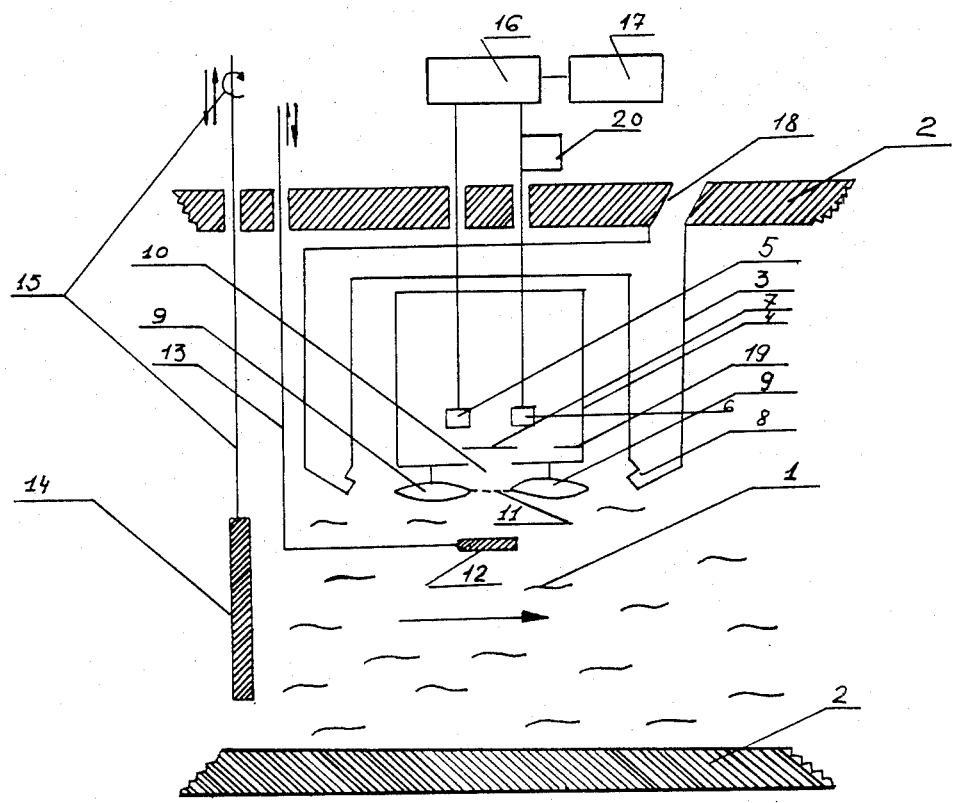

United States Patent [19]

Ab

[11] Patent Number: 4,490,832

[45] Date of Patent: Dec. 25, 1984

[54] TECHNIQUE AND APPARATUS FOR TWO-PHASE SYSTEMS ANALYSIS DIRECTLY IN A FLOW

[75] Inventor: Emil A. Ab, Jerusalem, Israel

[73] Assignee: Middle East Trade Alliance, Inc., Beverly Hills, Calif.

[21] Appl. No.: 397,043

[22] Filed: Jul. 12, 1982

[51] Int. Cl.³ ............................................. G01N 23/22
[52] U.S. Cl. ...................................... 378/47; 378/45
[58] Field of Search .......................................... 378/47

[56] References Cited

U.S. PATENT DOCUMENTS 3,256,431  6/1966  Fraser ................................... 378/47

Primary Examiner—Craig E. Church
Attorney, Agent, or Firm—Martin LuKacher

[57] ABSTRACT

Method and apparatus for X-ray spectrum analysis of flowing material, and particularly where the material has two phases such as a suspension. A flow of gas or floats are used to separate the flowing material from an X-ray window in a casing containing an X-ray source and detector, which casing is located directly in the stream of flowing material. The gas flow provides a protective curtain across the window. An electrode structure is moveably mounted adjacent to the window and enables the solid state phase to be deposited for separate analysis of the solid and liquid phases of the flowing material.

19 Claims, 1 Drawing Figure

TECHNIQUE AND APPARATUS FOR TWO-PHASE SYSTEMS ANALYSIS DIRECTLY IN A FLOW

It is well known that many technological processes call for periodic (and in some instances continuous) control over chemical composition of various materials in a flow, for example, liquids and two-phase systems, such as various suspensions, etc, comprising constituents which can differ in their state of aggregation and chemical composition as well.

In modern practice this problem is solved by the use of X-ray spectrum analyzers of specific design wherein part of the flow of the material under analysis is introduced into the analyzer measuring system via a by-pass line and through-flow cuvettes provided with windows. Said analyzers are of a more complicated design compared to quantometers used for solid material samples analysis, and feature a number of shortcomings resulting from their principle of operation.

The required cuvette window coverings made of films or membranes impose a limitation as regards to the elements to be analyzed, as even the thinnest of the films used for this purpose not always provide for adequate penetration of light elements radiation. Due to unavoidable vibration of said films, resulting from flow pressure fluctuations, the distance between the material under analysis and the analyzer transducer also varies; film thickness changes as well due to wear and because of deposition of solid phase particles on their inner surface. It is impossible to assess said changes and consequently to eliminate the resultant errors. As a separate analysis of both phases is not feasible, it is impossible to determine which part of the element under analysis is in a solid phase and which is in a liquid state. Variations in phase ratio call for development of a special technique for eliminating errors which otherwise will take place. In case an extremely high rapidity of analysis is required errors due to differences in main and by-pass flow velocities are possible. Low strength of thin films results in frequent failures and apparatus used in modern practice are provided with special devices for automatic replacement of damaged films by new ones. The cost of one such analyser is approx. $200,000, installation cost—in the order of $50,000. Said analyzers should be attended only by highly-skilled personnel.

The main object of the present invention is to propose a technique and apparatus for X-ray spectrum analysis of liquids and two-phase systems directly in a flow which are free from mentioned above shortcomings.

The main idea of the invention consists in changing the system of contact of the material under analysis with the analyzer. Instead of directing part of the flow through a by-pass line connected to the analyzer transducer it is suggested to place said transducer directly into the flow of the material under analysis, providing a gas (air) cushion is build up between the material flow and transducer window in order to protect said transducer from mechanical or any other damages. A gas cushion makes it possible to completely eliminate the necessity in any film for isolating the flow of material under analysis from said transducer. In order to be able to analyze both phases separately a periodic local electrophoresis in the immediate vicinity of the transducer is suggested. Such technique allows a complete elimination of the mentioned above shortcomings.

An arrangement designed for the proposed technique realization is presented in a schematic form in FIG. 1, where: 1—flow of material to be analyzed, 2—a pipeline wall, 3—an analyzer transducer outer casing, 4—an analyzer transducer inner casing, 5—a primary radiation source, 6—a secondary radiation detector, 7—an X-ray filter system, 8—nozzles for building up a gas cushion, 9—floats for fixing the distance between the material surface and transducer window, 10—a transducer inner casing window, 11—a grid made of current-conducting material, 12—a movable electrode made of conducting material, 13—an electrode holder, 14—a movable partition, 15—a partition shifting gear, 16—a power supply unit, 17—a recording unit, 18—a gas inlet and outlet branch pipe, 19—an emergency damper-type valve, 20—a preamplifier.

Said arrangement operates as follows: after the transducer is placed inside a closed pipeline and prior to operation gas (air) is to be introduced into the space between the transducer outer and inner casings 3 and 4, said gas being supplied via the nozzles 8 produces a gas (air) cushion between the flow 1 surface and the transducer window 10. When the flow is exposed to the source 5 (for example, a radioactive isotope) radiation, an X-radiation from the flow constituent chemical elements is induced, said X-radiation being detected by the detector 6 which sends signals to the recording unit 17 via the preamplifier 20. In order to prevent any variations in the distance between the flow surface and the transducer window a system of floats 9 is provided which is rigidly connected with transducer inner casing 4. To reduce variations in floats immersion with flow density to an admissible minimum, the shape of said floats should be adopted keeping in mind that for a given volume their cross-section has to be maximal. This ensures not a deep immersion and consequently negligibly small variations in the abovementioned distance.

When separate analyses of both phases are required the difference of potentials is supplied by the power supply unit 16 to the grid 11 and electrode 12 so that due to the electrophoresis the solid phase would be deposited on the electrode 12. In case the deposition process would be hindered by the material flow, said partition 14 can be shifted by means of the shifting gear 15 in such a manner that the flow in the immediate vicinity to the transducer will be retarded.

When the solid phase is deposited on the electrode 12 the liquid phase analysis can be carried out through the openings in the grid 11. Then by the use of the electrode holder 13 the electrode 12 is lifted towards the grid 11, up to the stop, voltage between them being previously cut off, and the analysis of the deposit, i.e. the solid phase, can be carried out through the openings in the grid 11. Thereupon the electrode 12 is lowered into its initial position by means of the electrode holder 13, the partition 14 also returns to its initial position and the analysis of the material as a whole can be continued or the cycle for separate analyses of both phases can be repeated. In the latter case a short interval (approx. 10 sec) is needed for cleaning of previous deposit from the electrode 12 surface. In order to speed up the process of washing off said deposit by the flow it is advisable to supply the difference of potentials between the grid 11 and the electrode 12, but for this purpose of opposite signs than in case of deposit formation.

When analysis of light elements producing their own radiation which is to a great extent absorbed by air is required, for building up a gas cushion helium or any other gas which absorbs said radiation to a very small extent should be used. In other cases ordinary air can be utilized for this purpose. The grid 11 can be employed as a monitor for control and automatic adjustment over the whole measuring path. For this purpose it is sufficient to make use of the own (secondary) X-radiation of the element said grid is made of. In case the flow of material under analysis is moving along an open trough or any other arrangement with the flow surface invariably open the analyzer transducer can operate with no gas (air) cushion provided, and the required space between the flow surface and the transducer window 10 is ensured by means of floats 9. Only when light elements are to be analyzed helium (or a similar gas) stream is required. In this case in order to reduce gas consumption it is advisable to carry the analysis out in a closed system. In case of a failure in the gas supply system the transducer casing window 10 is automatically closed by the emergency damper-type valve 19.

It is readily apparent that the proposed technique and apparatus for its realization make it possible to eliminate the sources of all the shortcomings which the existing analyzers for two-phase system analysis display. Elimination of any covering for the transducer window (or windows in case a number of transducers for carrying out analysis of a variety of elements simultaneously is required) solves all the related with said coverings problems, namely—strength of said coverings and their replacement, errors due to variations in thickness and vibration resulting from fluctuations in the flow pressure. The possibility of separate analyses of both phases to be carried out rules out the errors arising from variation in phase ratio and makes it possible to determine the distribution of same element along the phases. The problem of differences in main and by-pass flow velocities does not exist any more as no by-pass flow is required. The transducer as a whole can be moved in the direction normal to the flow direction, if there are reasons to believe that differences in chemical composition at various depths are possible. The proposed transducers are portable and comparatively cheap which enables them to be fitted in various points along the process line with the resultant enormous increase in information data obtained. The cost of the proposed arrangements of this type as compared to the cost of the existing quantometers, used for material analysis in a flow, is not less than one order lower, while the attendance they require is by far simpler. The power supply and recording units can operate practically under any conditions, therefore no special room provided with air conditioning is required, neither are great amounts of water and electric power required as opposed to cases when the existing apparatuses are used.

What I claim is:

1. Apparatus for X-ray spectrum analysis of flowing material having solid and liquid phases directly in a stream of such material comprising: a portable transducer placed directly inside said stream, power supply and recording units connected to said transducer and positioned outside said stream, said portable transducer comprising a casing with a window, a primary X-radiation source, a detector, X-ray filters, means for shifting said filters, a system of nozzles for producing a gas cushion across said window, a moveable flap covering said window in the absence of said cushion, a plane capacitor having two electrodes positioned parallel to said transducer window, wherein the one of said electrodes nearest to said transducer is a grid and the second of said electrodes is a solid plate, means for changing the distance between said electrodes, means for fixing said transducer inside said stream, means for shifting said transducer, a partition in said stream for retarding said flow, and means for changing the angle of rotation of said partition relative to flow direction of said stream.

2. The method of X-ray spectrum analysis of flowing material with the aid of X-ray spectrum analyser means in a housing having a window which comprises the steps of locating said housing with said window within the flowing material, and passing gas across said window to establish a cushion protecting said analyser means.

3. The method according to claim 2 further comprising closing said window with a flap until the protective gas cushion is formed.

4. The method according to claim 2 further comprising forming said protective gas cushion with gas selected from the group consisting of air and helium.

5. The method according to claim 2 wherein said flowing material has two phases, one of which is a solid phase and the other of which is a non-solid phase and further comprising the step of separating by electrophoresis said solid phase from said non-solid phase for separate X-ray analysis thereof.

6. The method of X-ray spectrum analysis of two-phase flowing material which comprises the steps of locating X-ray spectrum analysis means directly in said flowing material, separating said phases by electrophoresis to present the solid state of said material for analysis by said X-ray spectrum analysis means.

7. The method according to claim 6 wherein said X-ray and analysis means has a window for outward passage of primary X-rays and inward passage of secondary X-rays for detection therein, said separating step being carried out with the aid of an electrode by depositing said solid phase by electrophoresis on said electrode, analyzing the non-solid phase of said material and the solid phase of said material when said electrode is further and closer to said window, respectively.

8. The method according to claim 7 further comprising the step of retarding a part of the flow of said material over said electrode to increase the thickness of solid phase material deposited on said electrode by electrophoresis.

9. The method of X-ray spectrum analysis of flowing material with the aid of a spectrum analyser in a casing having a window for the outward passage of primary and inward passage of secondary X-rays which comprises the steps of placing said housing in a stream of said flowing material, and floating said housing on said material to space said window from said stream.

10. The method according to claim 9 wherein said flowing material has two phases one of which is a solid phase and the other of which is a non-solid phase and further comprising the step of separating by electrophoresis said solid phase from said non-solid phase for separate X-ray analysis thereof.

11. Apparatus for X-ray spectrum analysis of flowing material which comprises an X-ray spectrum analyser, a housing having a window containing said X-ray spectrum analyser, said housing being disposed with said window within said flowing material, and means for passing a gas across said window to establish a cushion protecting said analyser.

12. The apparatus according to claim 11 further comprising a flap moveably disposed for closing said window until said protective gas cushion is formed.

13. The apparatus according to claim 11 wherein the gas forming said window is selected from the group consisting of air and helium.

14. The apparatus according to claim 11 wherein said flowing material has two phases, one a solid phase and the other a non-solid phase and further comprising means for separating said solid phase from said non-solid phase for separate X-ray analysis thereof by electrophoresis separation.

15. Apparatus for X-ray spectrum analysis of two-phase flowing material which comprises X-ray spectrum analysis means disposed directly in said flowing material and means for separating the phases of said material by electrophoresis to prevent the solid state of said material to said analysis means for analysis separately from the non-solid phase of said material.

16. Apparatus according to claim 15 wherein said X-ray spectrum analysis means has a window for outward passage of primary X-rays and inward passage of secondary X-rays for detection, said separating means including an electrode on which said solid phase is deposited by electrophoresis, and means for moving said electrode with respect to said window to permit analysis of the non-solid phase of said material and the solid phase of said material when said electrode is further and closer to said window, respectively.

17. The apparatus according to claim 16 further comprising means for retarding a part of the flow of said material over said electrode to increase the thickness of solid state material deposited thereon by electrophoresis.

18. Apparatus for X-ray spectrum analysis of flowing material which comprises an X-ray spectrum analyser in a casing having a window for the outward passage of primary and the inward passage of secondary X-rays, floats disposed on said housing adjacent to said window and said housing being disposed on a stream of said flowing material with said floats floating said housing to space said window from said stream.

19. The apparatus according to claim 18 wherein said flowing material has two phases, one a solid phase and the other a non-solid phase and further comprising means for separating said solid phase from said non-solid phase for separate X-ray analysis thereof by electrophoresis separation.

* * * * *